United States Patent [19]

Taya et al.

[11] Patent Number: 4,614,748

[45] Date of Patent: Sep. 30, 1986

[54] TOPICAL USE COMPOSITION FOR THE TREATMENT OF SEBORRHEA AFFECTIONS OF THE HUMAN SCALP

[75] Inventors: Miguel M. Taya; René R. Sala, both of Barcelona, Spain

[73] Assignee: Rocador Sociedad Anonima, Spain

[21] Appl. No.: 300,424

[22] Filed: Sep. 8, 1981

[30] Foreign Application Priority Data

Feb. 19, 1981 [FR] France ............................. 81 03325

[51] Int. Cl.$^4$ .............................................. A61K 7/06
[52] U.S. Cl. .............................. 514/613; 424/DIG. 4; 424/70
[58] Field of Search .................. 424/320, DIG. 4, 70; 514/613

[56] References Cited

FOREIGN PATENT DOCUMENTS

| | | | |
|---|---|---|---|
| 1020865 | 11/1977 | Canada ................................ | 424/320 |
| 1238619 | 4/1967 | Fed. Rep. of Germany ...... | 424/320 |
| 2004647 | 8/1971 | Fed. Rep. of Germany ...... | 424/320 |
| 2351821 | 4/1975 | Fed. Rep. of Germany ...... | 424/320 |
| 1163386 | 4/1958 | France ................................ | 424/320 |
| 2301232 | 9/1976 | France ................................ | 424/320 |
| 1015261 | 12/1965 | United Kingdom ............... | 424/320 |

*Primary Examiner*—Dale R. Ore
*Attorney, Agent, or Firm*—Sughrue, Mion, Zinn, Macpeak, and Seas

[57] ABSTRACT

The purpose of the invention is a composition for the treatment of affections of the human scalp caused by seborrhea.

According to the invention the composition is characterized in that it contains N-hydroxyethylacetamide as active ingredient.

13 Claims, No Drawings

TOPICAL USE COMPOSITION FOR THE TREATMENT OF SEBORRHEA AFFECTIONS OF THE HUMAN SCALP

FIELD OF THE INVENTION

The present invention relates to compositions useful in combatting affections caused by seborrhea on the human scalp. More particularly, this invention is concerned with compositions constituted by or containing N-hydroxyethylacetamide as active ingredient.

SUMMARY OF THE INVENTION

This compound, which is already known, is also known under the scientific name of N-acetylethanolamine; and has the following formula:

$$CH_3-CO-NH-C_2H_4OH$$

and it is presented in form of a viscous liquid at room temperature. The density of this product (DIN/20° C.) is 1.12 and the molecular weight thereof is 103. The boiling point thereof is 155° C. under an absolute pressure of 5 mm Hg.

Several processes are known for the preparation of this compound. The following may be cited from among these: one mole of acetyl chloride is poured carefully over a solution of 2 moles of monoethanolamine in methylene chloride. The mixture is cooled over ice bath during this addition. The mixture is stirred for two hours and filtered. The solvent is removed by distillation at atmospheric pressure and thereafter in vacuo (5 mm Hg), thus leading to the separation of the N-hydroxyethylacetamide.

As said above, N-hydroxyethylacetamide has been described and known for many years. It is used as raw material in organic synthesis, as solvent and, in view of its well known harmlessness, as vehicle in the formulation of injectable drugs.

The invention is based on the fact that, surprisingly, when N-hydroxyethylacetamide is applied directly or forms part of a liquid composition, it allows affections caused by seborrhea on the human scalp to be successfully combatted. As is known, dandruff (dry or greasy) are frequently formed on the human scalp, namely, greasy layers of the horny layer of said scalp, which break away by desquamation in form of scales. This dandruff-formation is due to seborrhea or to an abnormal secretion of grease by the sebacic glands of the scalp.

The appearance of the dandruff is normally accompanied by falling of the hair. Independently of the fact that it is the cause of the appearance of dandruff, the seborrhea also alters the correct nutrition of the hair and, thus, seborrhea may also cause seborrheic baldness (alopecia), that is, the falling of the hair, even in the case when the said dandruff are not formed.

Through countless experiments, it has been observed that the repeated application of N-hydroxyethylacetamide to the scalp is suitable for eliminating the presence of any dandruff, after only a few days. Simultaneously it reduces the loss of hair in very many cases. Moreover, when application is continuous, it acts against the seborrheic alopecia or baldness stimulating the growth of new hairs.

N-hydroxyethylacetamide is used in an alcoholic or aqueous solution and, preferably, in an aqueous alcohol solution at concentration levels lying between 2.5 and 5%.

When the composition in question is used for scalp frictions, it corrects the seborrhea by regulating the secreting function of the scalp sebacic glands. Thanks to this, the dandruff disappear and falling hair is avoided. As has already been pointed out, the phenomena of appearance of dandruff and falling hair may exist side by side or not.

The above composition may cause the growth of new hairs when applied to follicles which have not lost their vitality. To the regularisation of the grease secretion there is added a good nutrition of the hair and, thus, the recovery of the latter.

EXAMPLE 1

A 2.5% N-hydroxyethylacetamide lotion was prepared in 75 volumes of ethyl alcohol and 25 volumes of water.

The said lotion was applied to 5 persons suffering from dandruff and abundant falling hair twice daily by friction on the scalp. Twenty four hours after the first friction, in all the treated patients, the dandruff were observed to have disappeared, together with a cessation of the falling of the hair.

EXAMPLE 2

A 5% N-hydroxyethylacetamide lotion was prepared in 75 volumes of ethyl alcohol and 25 volumes of water.

The said lotion was administered twice daily by scalp friction to 3 persons close on 50 years old who had been suffering from seborrheic alopecia for a long time. One month and a half after the start of treatment, groups of hairs spread out over the bald surface were observed and the hair thereafter developed normally.

As will be observed and as results moreover from the foregoing, the invention is not restricted to those forms of application that have been particularly contemplated; on the contrary, it embraces all the variations.

What we claim is:

1. A topical use composition for the treatment of seborrhea and dandruff affections of the human scalp, characterised in that the composition contains a therapeutically effective amount of N-hydroxyethylacetamide as active ingredient.

2. A topical use composition for the treatment of seborrhea and dandruff affections of the human scalp, characterised in that the composition contains at least one active ingredient constituted by a therapeutically effective amount of N-hydroxyethylacetamide.

3. The composition of claim 2, characterised in that the N-hydroxyethylacetamide is in aqueous or alcoholic solution.

4. The composition of claim 2, characterised in that the N-hydroxyethylacetamide is in aqueous alcohol solution.

5. The composition of claim 3 and 4, characterised in that the solution contains from 2.5 to 5% of N-hydroxyethylacetamide.

6. The composition of claim 4, characterised in that the aqueous alcohol solution comprises 75 volumes of ethyl alcohol and 25 volumes of water.

7. Hair lotion characterised in that it comprises from 2.5 to 5% of N-hydroxyethylacetamide in aqueous alcohol solution.

8. The hair lotion of claim 7, characterised in that the aqueous alcohol solution is 75 volumes of ethyl alcohol and 25 volumes of water.

9. A process for the treatment of seborrhea and dandruff affections of the human scalp, comprising application of a therapeutically effective amount of N-hydroxyethylacetamide to the scalp.

10. A process as in claim 9, wherein the N-hydroxyethylacetamide is applied to the form of an aqeous or alcoholic solution.

11. A process as in claim 9, wherein the N-hydroxyethylacetamide is applied in the form of an aqueous alcohol solution.

12. A process as in claim 11, wherein the aqueous alcohol solution comprises 75 volumes of ethyl alcohol and 25 volumes of water.

13. A process as in claim 10, 11, or 12, wherein the solution contains from 2.5 to 5% of N-hydroxyethylacetamide.

* * * * *